US012564314B2

(12) United States Patent
Do et al.

(10) Patent No.: US 12,564,314 B2
(45) Date of Patent: Mar. 3, 2026

(54) ENDOSCOPE WITH VARIABLE STIFFNESS

(71) Applicant: AMBU A/S, Ballerup (DK)

(72) Inventors: Anh Minh Do, Munich (DE); Manfred Josef Großhardt, Königsbrunn (DE)

(73) Assignee: AMBU A/S, Ballerup (DK)

( * ) Notice: Subject to any disclaimer, the term of this patent is extended or adjusted under 35 U.S.C. 154(b) by 258 days.

(21) Appl. No.: 18/598,341

(22) Filed: Mar. 7, 2024

(65) Prior Publication Data

US 2024/0298885 A1 Sep. 12, 2024

(30) Foreign Application Priority Data

Mar. 10, 2023 (EP) ..................................... 23161212

(51) Int. Cl.
*A61B 1/005* (2006.01)
*A61B 1/00* (2006.01)
*A61M 25/01* (2006.01)

(52) U.S. Cl.
CPC .......... *A61B 1/0055* (2013.01); *A61B 1/0011* (2013.01); *A61B 1/00128* (2013.01); *A61B 1/0052* (2013.01); *A61B 1/0057* (2013.01); *A61B 1/00009* (2013.01); *A61B 1/00045* (2013.01); *A61M 25/0136* (2013.01); *A61M 25/0138* (2013.01); *A61M 25/0147* (2013.01)

(58) Field of Classification Search
CPC .................... A61B 1/00078; F16H 2025/2059
See application file for complete search history.

(56) References Cited

U.S. PATENT DOCUMENTS

| | | | |
|---|---|---|---|
| 4,977,887 A * | 12/1990 | Gouda | ............... A61B 1/00071 |
| | | | 600/140 |
| 5,885,208 A | 3/1999 | Moriyama | |
| 5,976,074 A | 11/1999 | Moriyama | |
| 6,203,494 B1 | 3/2001 | Moriyama | |
| 2002/0004627 A1 | 1/2002 | Takase | |
| 2017/0127910 A1 | 5/2017 | Asaoka et al. | |
| 2018/0249892 A1* | 9/2018 | Okaniwa | ............ A61B 1/00078 |
| 2020/0297188 A1* | 9/2020 | Ikeda | .................... A61B 1/0053 |
| 2020/0323421 A1* | 10/2020 | Okaniwa | ............ A61B 1/00135 |
| 2020/0352412 A1* | 11/2020 | Saito | ....................... A61B 1/018 |
| 2022/0273162 A1* | 9/2022 | Hosogoe | .............. A61B 1/0057 |

FOREIGN PATENT DOCUMENTS

| | | |
|---|---|---|
| JP | H1033464 A | 2/1998 |
| JP | H1156764 A | 3/1999 |
| JP | 2002000554 A | 1/2002 |

(Continued)

OTHER PUBLICATIONS

Extended search report in European application No. 23161212.8, Aug. 16, 2023, 8 pages.

*Primary Examiner* — Michael J Carey
*Assistant Examiner* — Stephen Floyd London
(74) *Attorney, Agent, or Firm* — Faegre Drinker Biddle & Reath LLP

(57) ABSTRACT

An endoscope having a proximal handle and a flexible insertion cord extending in distal direction from the handle, and further provided with an insertion cord stiffener. The stiffener includes a coil and a wire extending through the coil and being attached to the coil at the coil distal end. A control at the handle operates the stiffener by tensioning the wire.

17 Claims, 6 Drawing Sheets

(56)         References Cited

FOREIGN PATENT DOCUMENTS

| JP | 2002253476 | A |   | 9/2002 |   |   |
|----|------------|---|---|--------|---|---|
| JP | 2002369791 | A |   | 12/2002 |  |   |
| JP | 2003260021 | A | * | 9/2003 | ......... | A61B 1/00078 |
| JP | 3776816 | B2 |   | 5/2006 |   |   |
| JP | 4681753 | B2 |   | 5/2011 |   |   |
| JP | 6153911 | B2 |   | 6/2017 |   |   |

* cited by examiner

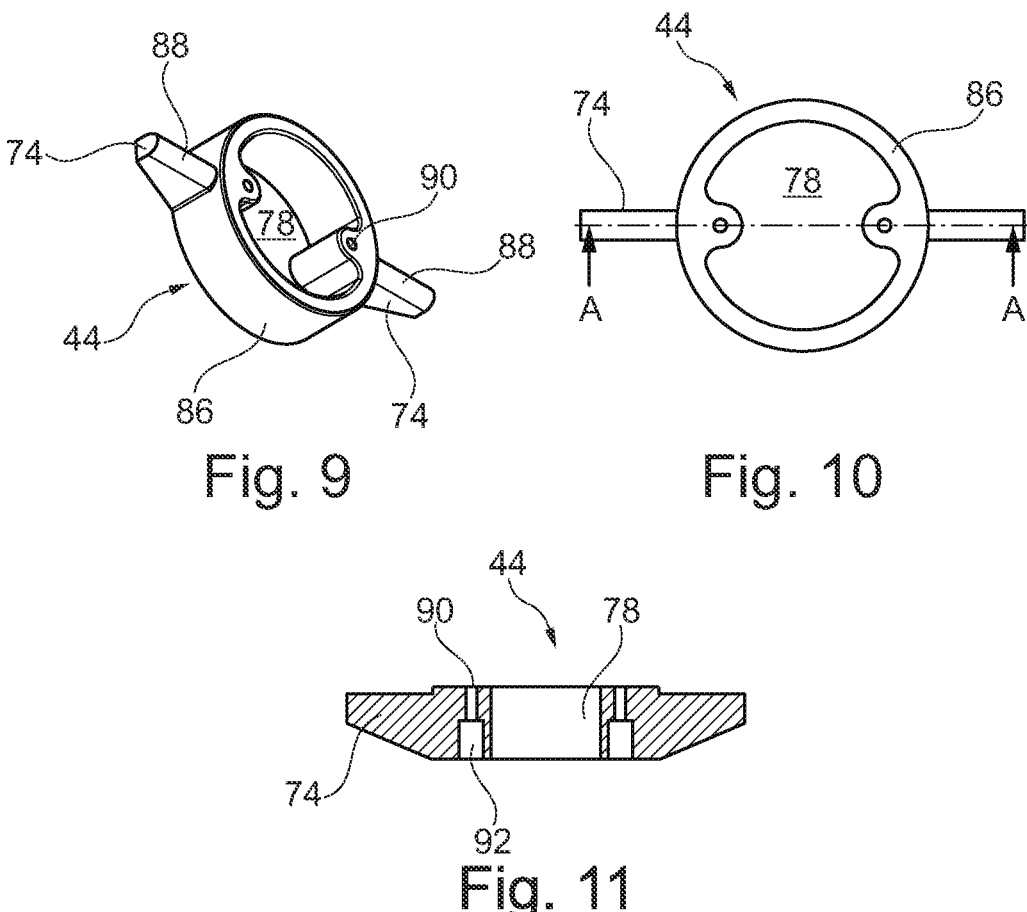
Fig. 9
Fig. 10
Fig. 11
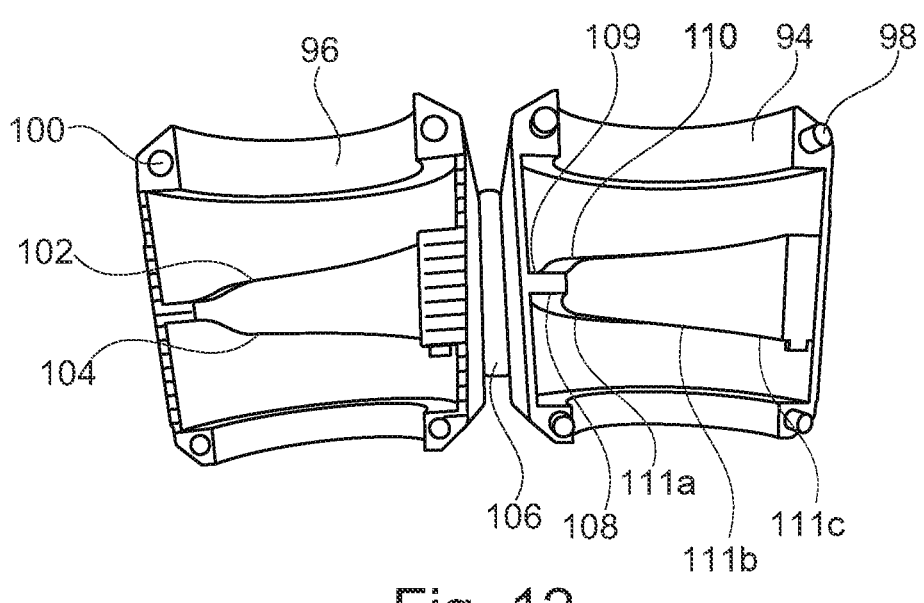
Fig. 12

120a

120b

120c

122

134

130

136

132

138

8

7

62

20

ENDOSCOPE WITH VARIABLE STIFFNESS

CROSS-REFERENCE TO RELATED APPLICATIONS

This application claims priority from and the benefit of European Patent Application No. EP 23161212.8, filed Mar. 10, 2023; the disclosure of said application is incorporated by reference herein in its entirety.

TECHNICAL FIELD

The present invention relates to endoscopes, and in particular flexible endoscopes with variable stiffness.

BACKGROUND

Endoscopes are known and used for visual navigation into, and examination and diagnosis of, hollow organs and body cavities, as well as, optionally, to assist in surgery, e.g. for a targeted tissue sampling. Endoscopes include procedure-specialized endoscopes, such as gastroscopes and colonoscopes. Endoscopes may comprise a handle at the proximal end to be gripped by an operator and a flexible, elongated insertion cord extending distally from the handle. The insertion cord may include an insertion tube terminated in a distal tip part at the end of a highly bendable, e.g. articulated, bending section controllable by the operator. The tip part may comprise an observation optical system extending distally from the bending section.

The controllable bending section may be an articulated section at the distal tip of the elongated insertion cord. The bending section may be controlled by the operator via a control wheel arranged on the handle. The control wheel may be connected to the bending section by a steering wire. Pulling a steering wire may bend the bending section in one direction. A number of steering wires may be provided to bend the bending section in a given direction to direct the distal tip in a certain direction, such as in two opposite directions or in four directions, e.g. two opposite directions in a first plane and two opposite directions in a second plane at right angles to the first plane.

Thus, using the control wheels allows the operator to advance the distal tip of the endoscope to a desired location by means of a series of actions involving inter alia bending the bending section in a desired direction, advancing the elongated insertion cord, and twisting the elongated insertion cord.

Navigating a tortuous path of bends and turns to a location of interest requires some flexibility of the insertion cord. Procedures using flexible endoscopes may however require some force from the operator and forwarding the endoscope through body cavities may be difficult because of the flexibility, which may give rise to buckling and loop formation of the insertion cord because of limited column strength. For example, in case of a colonoscopy, the operator inserts the insertion cord of a colonoscope through the rectum and colon of a patient. Peristaltic movements of the colon may, however, work against forwarding the colonoscope, and gravitational forces acting on the insertion cord may also influence the ability to forward the colonoscope through the tortuous path of the colon, which has some sharp bends. The flexibility of the insertion cord may here be disadvantageous, as it may be difficult for the operator to transmit force and torque to the distal end of the insertion cord, leading to difficulties in forwarding the endoscope, especially to get past the bends of colon. These difficulties lead to straining work conditions and strain on the operator, and further time consumption of the procedure may be high, which increases the cost of the procedure and may negatively influence comfort for the patient. Colonoscopy is often perceived by patients as inconvenient and painful.

A compromise between flexibility and stiffness of the insertion cord is difficult to achieve and further the optimum flexibility may change during the procedure, or different operators may prefer different flexibility. Operators try to prevent or solve difficulties in advancing the endoscope by applying different techniques, such as applying abdominal hand pressure, twisting the flexible insertion cord, repositioning the patient, and frequently pulling back the flexible insertion cord to straighten it again. Insertion of a flexible insertion cord e.g. in the colon is difficult to master because of the compliant nature of the colon and the fact that it is usually not possible to see how the insertion cord behaves inside the colon of the patient, so it takes about 150 practice procedures to obtain reasonable endoscope insertion skills.

There is a rising demand for single-use endoscopes as they are always at hand being sterile out of the pack, so for each patient a new sterile endoscope is used, whereas reusable endoscopes need rigorous reprocessing before use for each patient, plus possible repair and testing. Hence the reusable endoscope will often not be available. Single-use endoscopes offer complete cost transparency, involve low investment relative to reusable endoscopes, provide consistent quality, and eliminate the risk of cross-contamination. Cleaning and reprocessing of re-usable endoscopes have a major environmental impact in view of energy, water and chemicals used, which may further negatively influence performance of the endoscope, so single use endoscopes can be a sustainable solution in view of choice of materials and the fact that no cleaning and reprocessing of the used endoscope is needed.

For single-use endoscopes, it is important that the entire device is manufactured in a cost-efficient way. For this reason, single use endoscopes are mainly made of polymeric materials to enhance disposability and reduce costs.

It is desirable to improve versatility of endoscopes, particularly in single-use endoscopes, to increase their value.

BRIEF DESCRIPTION OF THE DISCLOSURE

The objective of the present disclosure is to provide an endoscope with features that eliminate or at least reduce the disadvantages of prior art endoscopes and suitably deal with the problems described above. In particular, an endoscope shall be provided, which is designed for single use and which has an insertion cord stiffener made of commercially available and low-cost material. A further objective is to provide a suitable method for manufacturing an endoscope.

A first aspect of this disclosure relates to an endoscope comprising a handle and a flexible insertion cord extending distally from the handle, an insertion cord stiffener comprising a coil, a wire connected to a distal end of the coil, and a stiffener control comprising a rotatable control ring. Rotation of the control ring changes tension in the wire and causes the coil to tension or relax, thereby changing the stiffness of the insertion cord.

In an embodiment according to the first aspect of this disclosure, the endoscope further comprises: a coil anchor at the handle; a wire anchor at the handle, the proximal coil end abutting the coil anchor and the coil extending into the insertion cord; the wire extending through the coil and being connected to the coil at the coil distal end, the proximal wire end being connected to a wire anchor; the rotatable control ring having a rotation axis approximately parallel to the longitudinal direction of the handle, the control ring having an inner side with a helical engagement surface, wherein at least one of the wire anchor or coil anchor comprises at least one anchor arm engaging the helical engagement surface, wherein the handle comprises an anchor guiding surface engaging the at least one of the wire anchor or coil anchor restricting movement thereof to a direction parallel to the rotation axis. By parallel direction should be understood a direction deviating by up to 10 deg.

By providing an endoscope as described above it is achieved that variable stiffness functionality of the insertion cord can be provided even for single use endoscopes. The insertion cord stiffener can be provided as a self-contained unit, which does not require major change of the endoscope construction as forces acting on the insertion cord stiffener need not be transferred to the insertion cord or the handle, as tension of the wire is made by the control ring, which may take the load as compression force on the control ring external to the handle. Hence no reinforcements of the handle or other parts are necessary.

The control ring may have an external side with a surface configured for gripping and turning by hand to facilitate easy operation of the variable stiffness functionality.

The control ring may comprise only one helical engagement surface, such as a proximal helical engagement surface, in engagement with the wire anchor. In a variation of the present embodiment, however, the control ring comprises a proximal helical engagement surface in engagement with the wire anchor, referred to also as a "wire anchor engagement surface," and a distal helical engagement surface in engagement with the coil anchor, referred to also as a "coil anchor engagement surface," the proximal and distal engagement surfaces having opposite direction. By opposite direction it is meant that one engagement surface is inclined in one direction and the other engagement surface inclined in the opposite direction relatively to a cross sectional plane at right angles to the rotation axis similar to a left-hand thread and a right-hand thread. Opposite directions may be referred to as having "opposite handedness." Hereby is achieved that the control ring is double-acting in that the coil anchor and the wire anchor are forced away from each other simultaneously.

In a simple version of the control ring the helical engagement surface has a constant pitch. However, the pitch of the helical engagement surface does not need to be constant and may vary along the length of the control ring, such as a first pitch at an initial position and second pitch at an end position, where the first pitch is higher than the second pitch. Hereby is achieved that a park position is provided at the initial position, and a quick initial activation of the stiffener is provided, whereas the lower pitch at the end position limits the torque necessary to overcome forces and friction to turn the control ring at maximally activated state of the stiffener. In another example, the pitch of the helical engagement surface (either or both of the coil anchor engagement surface and the wire anchor engagement surface) varies along the length of the control ring, such as a first pitch at an initial position, a second pitch at an intermediate position, and a third pitch at an end position, where the first pitch is higher than the third pitch and may be higher than the second pitch.

The wire anchor and coil anchor could function with only one arm each, which would enable a longer travel of the control ring, which could then be allowed to travel 360° or nearly so. A downside would be uneven and unbalanced load, which might negatively influence other parts of the endoscope, such as the handle. Alternatively three or four arms could be provided on each anchor, which would decrease the load on each arm, but this would decrease the possible travel of the control ring. According to an embodiment the wire anchor and coil anchor each comprises two arms, which is considered to be a reasonable compromise and giving a balanced load on the parts.

The wire anchor may be assembled of different parts, e.g. by having separate arms, but it is considered favourable that the wire anchor is of unitary construction. Hereby cost of production and assembly can be kept low, and load and forces distributed in the entire construction.

Any one of the wire anchor, the coil anchor and control ring may be made fully or in part of any suitable material, such as stainless steel. For single use endoscopes, it is however preferred that the coil anchor, the wire anchor and the control ring are all made of polymeric material, such as plastic material, e.g. polyamides or ABS. Hereby the cost and impact on the environment can be kept low.

The length of the insertion cord of the endoscope can be for example 1300 to 1600 mm in the event of colonoscopes. For some endoscopes it may suffice with a relatively short stiffener, such as 300 to 400 mm, however it is generally preferred that the coil extends through a majority of the insertion cord, such as more than 50% of the insertion cord, e.g. more than two thirds of the length of the insertion cord. On the other hand it may be preferred that the stiffener extends through such less than 90% of the insertion cord, as it may be beneficial that the stiffener ends some distance before the bending section of the endoscope, such as 200 to 400 mm short of the bending section, e.g. 300 mm to keep a flexible distal end of the insertion cord.

According to an embodiment the endoscope comprises a second insertion cord stiffener. Hereby a higher stiffness of the endoscope insertion cord may be provided with limited extra cost. Further providing two insertion cord stiffeners may take up less space in the insertion cord compared to one big insertion cord stiffener. The two insertion cord stiffeners could have the same length, but could also differ in length e.g. to provide a stepwise graduated stiffness.

According to a variation of the present embodiment and variations thereof described above and below, the coil is made of wires having a cross-section selected from circular, rectangular, a parallelogram, trapezoid, or square.

The coil may be made of any suitable material, however according to an embodiment the coil is made of metal, such as stainless steel, which may have long shelf life without changes to the physical properties, such as due to creep.

It is conceivable to provide a solution where the wire anchor is arranged distal to the coil anchor, e.g. using a gear mechanism or a pulley, however a simple solution can be provided wherein the wire anchor is arranged proximal to the coil anchor.

A second aspect of the invention relates to a visualization system comprising an endoscope according to the first aspect and further comprising an image sensor; and a video processing apparatus capable of processing a video or image signal received from image sensor and outputting the processed video or image signal to a coupled display module, such as for example a medical monitor or a built-in display. The monitor may include a medical device interface configured to interface with the endoscope to receive a video or image signal captured by the image sensor.

A third aspect of the invention relates to a method for manufacturing an endoscope, comprising the steps of providing a first handle shell, providing an insertion cord, providing an insertion cord stiffener comprising a coil, a wire, a wire anchor, a coil anchor and a control ring, arranging the coil to extend into the insertion cord, arranging the coil anchor and the wire anchor in the first handle shell, providing a second handle shell, connecting the second handle shell to the first handle shell, arranging the control ring to encircle the first and second handle shell, and engaging the control ring to at least one of the wire anchor or coil anchor.

BRIEF DESCRIPTION OF THE DRAWINGS

The disclosure will now be made in greater detail based on non-limiting exemplary embodiments and with reference to the schematic drawings on which:

FIG. 9 is a perspective view of an anchor of the variable stiffness system, FIG. 10 is a plan view of the anchor of FIG. 9, FIG. 11 is a cross-sectional view along A-A of FIG. 10, FIG. 12 is a photo of a control ring prototype showing the inside thereof.

DETAILED DESCRIPTION

In the following the term "distal" refers to a position farthest away from the user, whereas the term "proximal" refers to the end closest to the user when using the endoscope in a patient.

Figure 1:
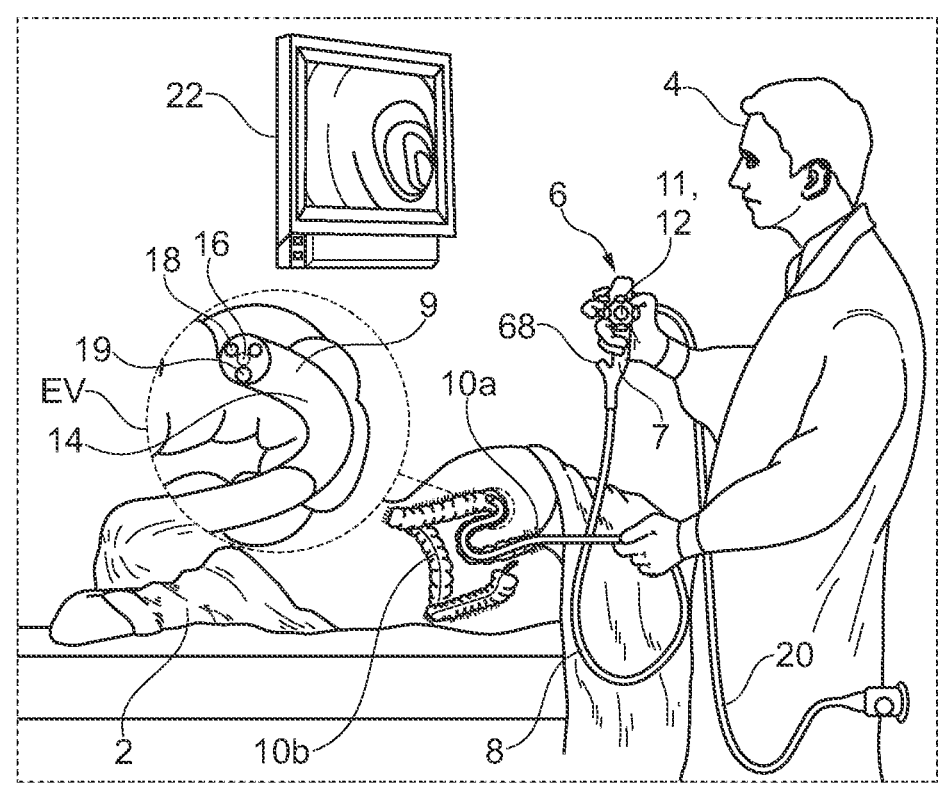
FIG. 1 depicts a colonoscopy procedure.

The general setup during a colonoscopy is illustrated in FIG. 1 showing an operating room with a patient 2 and an operator 4 using an endoscope 6. The endoscope 6 has a proximal handle 7 held by the operator 4 and a flexible insertion cord 8 with a distal tip 9 insertable into the rectum 10a and colon 10b of the patient 2. The internal path of the rectum and colon of the patient is illustrated as well as an enlarged view EV of the endoscope distal tip 9 inside the colon 10b. The handle 7 comprises control wheels 11, 12 connected via steering wires (not shown) to a bending section 14 at the distal end of the endoscope 6. The distal tip 9 of the endoscope 6 is equipped with camera 16 and light 18 (e.g. an LED or optical fibre) and possible further functions, such as openings for water, insufflation gas, suction or exit of tools. Reference number 19 indicates an opening. The camera can be an image sensor. The endoscope handle comprises control buttons and valves for operating camera, light and auxiliary functions, as well as an opening 68 for access to a working channel inside the insertion cord, e.g. for advancing tools to the distal tip of the insertion cord. An umbilical cord 20 connects the endoscope 6 to other equipment, such as monitor 22, power source, water and gas supply (not shown). Live images from the camera 16 at the distal tip of the endoscope is shown on the monitor 22. The patient lies on the side and the insertion cord of the endoscope is inserted into the rectum and colon of the patient.

Figures 2A, 2B, 2C:
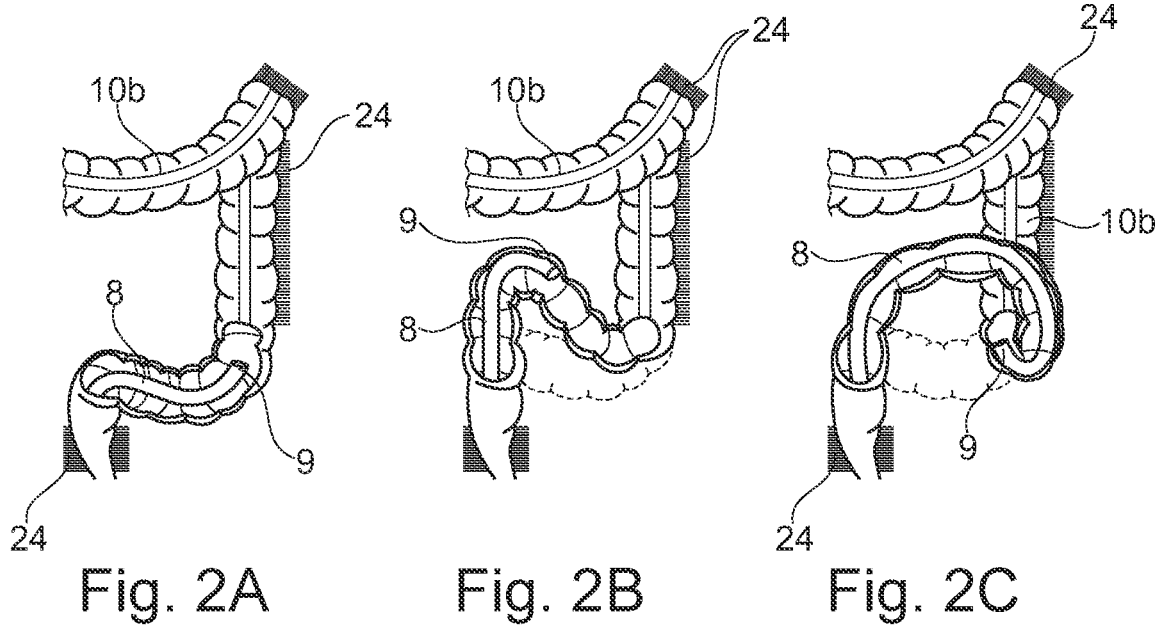
FIG. 2A illustrates an ideal situation where the flexible endoscope follows the curves of the colon.
FIG. 2B illustrates a common situation where the flexible endoscope pushes against the colon and stretches it.
FIG. 2C illustrates a typical loop shape that can occur during colonoscopy.

FIGS. 2A-2C illustrate insertion of the flexible insertion cord 8 into the rectum 10a and through the colon 10b. Position of some segments of the colon is fixed by ligaments 24, whereas other segments of the colon are not fixed by ligaments 24, so the position and shape of these segments of the colon are varying when the insertion cord is inserted, as schematically illustrated in FIGS. 2B and 2C. FIG. 2A illustrates the ideal situation with the flexible endoscope insertion cord 8 following the curves of the colon 10b. FIG. 2B illustrate the typical situation in practice: the endoscope distal tip 9 pushes against the colon 10b and stretches it until the colon 10b and its surroundings provide enough resistance to force the endoscope insertion cord 8 to bend. FIG. 2C illustrates a typical loop shape of the flexible insertion cord 8 that can occur. Because of the sharp bend at the distal tip 9, the flexible insertion cord 8 cannot advance, and the operator will need to pull back the insertion cord 8 to straighten it again.

Figures 3, 4, 5, 6:
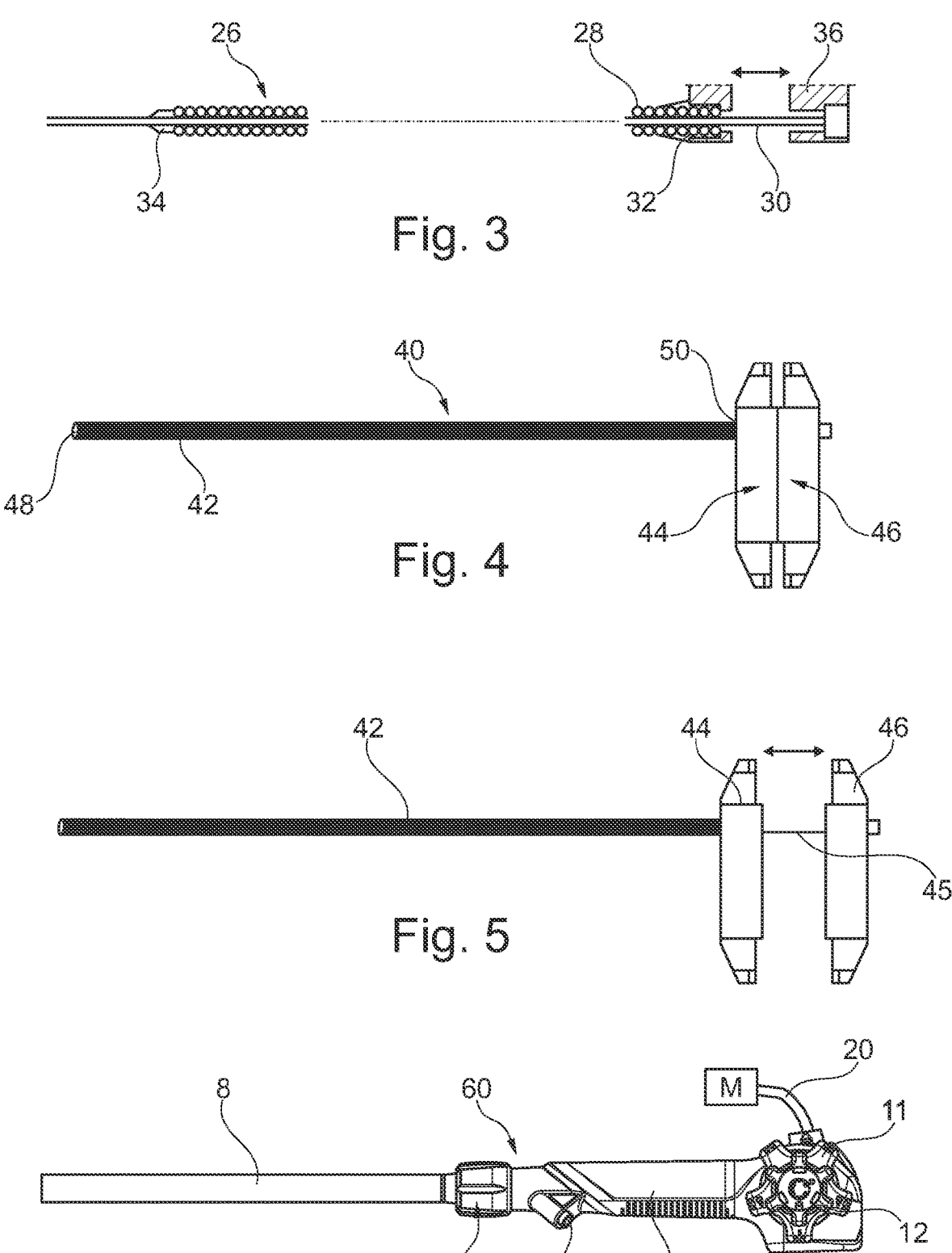
FIG. 3 is a schematic drawing of a stiffener.
FIG. 4 shows a stiffener according to a first embodiment in a first position.
FIG. 5 shows the stiffener of FIG. 4 in a second position.
FIG. 6 is a side view of an endoscope comprising a variable stiffness control.

An elementary sketch of a stiffener 26 in cross section (and a middle part illustrated by broken line) is shown in FIG. 3. The stiffener 26 is made up of a coil 28 and a wire 30 extending through the coil 28. A proximal end 32 of the coil 28 is fixed, whereas a distal end 34 is free. The wire 30 is connected to the coil 28 at the distal end 34 of the coil, whereas the proximal end of the wire is connected to a sleigh 36. The principle used is that in the relaxed state the coil 28 is relatively soft, i.e. not stiff, but instead will bend easily, whereas the coil can be put under tension by the wire 30, thereby stiffening the coil 28. This is the case if in the illustrated example the wire sleigh 36 is moved to the right, thereby pulling the wire 30, which in turn compresses and stiffens the coil 28. The compressed and stiffened coil 28 will resist bending.

Whereas FIG. 3 explains the general function of a stiffener without details on how to activate the stiffener, FIGS. 4 and 5 illustrate a stiffener 40 according to an embodiment of the disclosure with details for implementation as will be explained in the following. The stiffener 40 comprises a coil 42 (schematically illustrated), a coil anchor 44, a wire 45 (not shown, as it is inside the coil) and a wire anchor 46. A distal end 48 of the coil is free, whereas a proximal end 50 of the coil abuts the coil anchor 44. The wire 45 is connected to the distal end 48 of the coil 42, whereas a proximal end of the wire is connected to the wire anchor 46. Illustrated here is the relaxed state where the wire anchor abuts the coil anchor, meaning that the wire is not tensioned, and the coil hence uncompressed and flexible.

The stiffened state of the stiffener 40 is shown in FIG. 5. As can be seen the wire anchor 46 and coil anchor 44 are spaced apart, meaning that the wire 45, which is connected to the coil 48 at the distal end, is under tension, and the coil 48 compressed to provide a stiffened state of the coil 48.

An endoscope 60 according to an embodiment of the disclosure comprising a stiffener is schematically illustrated in FIG. 6. The endoscope comprises a handle 7 equipped with control wheels 11, 12, an umbilical cord 20 for connecting to auxiliary equipment, such as a monitor M, power source etc, and an insertion cord 8. A control ring 62 is arranged at the handle 7 for manipulation of the stiffener arranged inside the handle 7 and the insertion cord 8, as illustrated in more detail below. It should be understood that the endoscope shown is for illustration purposes only and not to scale. For example, the insertion cord will normally be much longer than apparent from FIG. 6.

Figure 7:
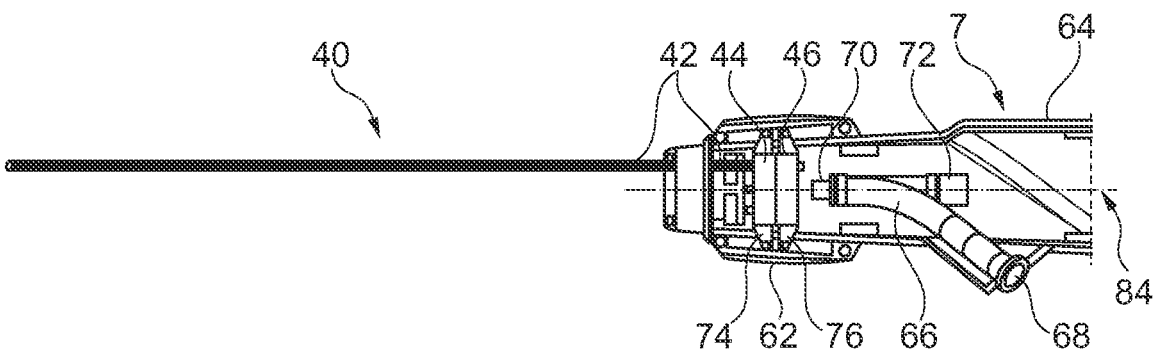
FIG. 7 shows part of the endoscope of FIG. 6 with parts removed for illustration of the variable stiffness system.
Figure 8:
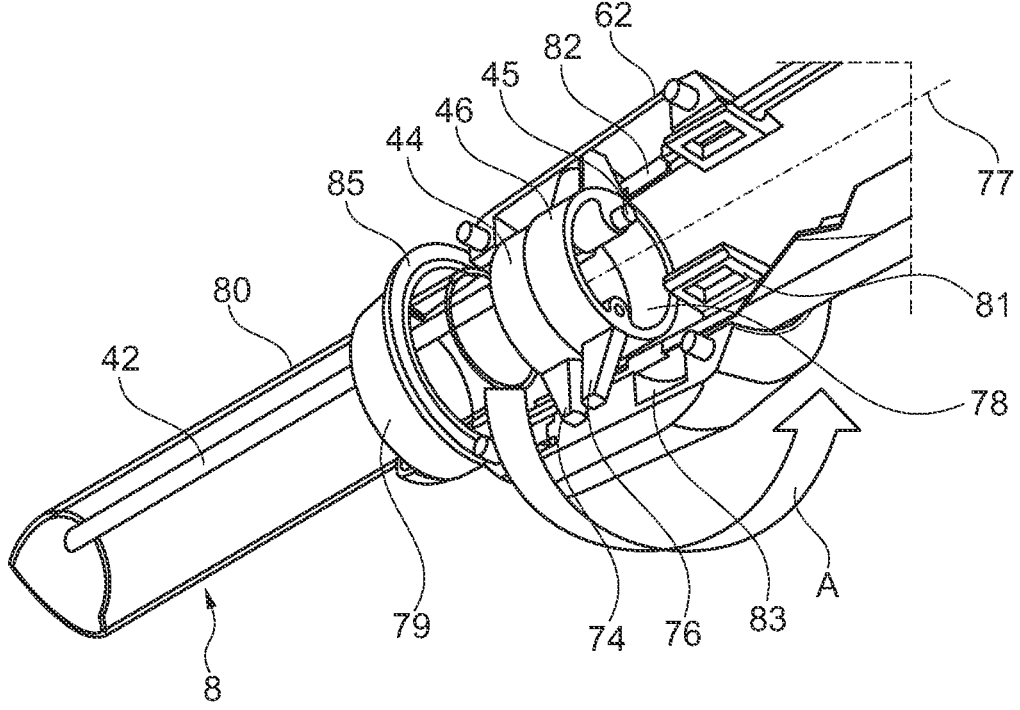
FIG. 8 is a perspective view of the endoscope of FIG. 7.

FIGS. 7 and 8 reveal the internal structure of part of the endoscope 60 of FIG. 6, where some parts are removed for simplification. A handle shell 64 of the handle 7 is shown, as well as a Y-connector 66 with an opening 68 at the handle, a connector 70 for a working channel (not shown), and a connector 72 for a suction tube (not shown). The stiffener 40 of FIG. 4 is here arranged in the handle shell 64 and the coil 42 is extending distally from the handle 7. The coil anchor 44 and wire anchor 46 are arranged in the handle shell 64 with coil anchor arms 74 and wire anchor arms 76 extending through the side wall of the handle shell 64 to the exterior thereof. The control ring 62 is arranged outside the handle shell 64. The handle is made up of two handle shells 64, which in the assembled state are held together by snaps 81 and a hoop 79. The handle 7 has the general shape of a cylinder or a truncated cone in this part of the handle and having a central axis 77. The inner side of the control ring is in engagement with the anchor arms 74, 76, as will be discussed in more detail with reference to the perspective view of FIG. 8 showing the same embodiment. The wire anchor 46 and coil anchor 44 are both generally ring shaped with a central opening 78 for a working channel, steering wires, electrical wires etc. extending into an insertion tube 80 of the insertion cord 8. The coil anchor arms 74 and wire anchor arms 76 extend through a slot 82 of the handle shell 64 and engage helical engagement surfaces 83 at the inside of the control ring 62. The control ring 62 is rotatable around the handle 7 with a rotation axis 84 coinciding or approximately parallel with the central axis of the handle 77. The control ring 62 bears on a proximal shoulder 85 of the hoop 79. The control ring 62 may hence be rotated around the handle, as illustrated by arrow A. When the control ring 62 bears on a proximal shoulder 85 of the hoop 79 it does not translate longitudinally.

Due to the opposite handedness of the engagement surfaces, the coil anchor 44 and the wire anchor 46 move away from each other upon rotation of the control ring 62 in a first direction. This may cause the coil 42 to translate inside the insertion cord 40 when the control ring 62 bears on the proximal shoulder 85 of the hoop 79. Upon rotation of the control ring 62 in a second, opposite to the first, direction, the tension in the coil and the wire cause the coil anchor 44 and the wire anchor 46 to move toward each other. In one variation, the coil anchor and wire anchor engagement surfaces are comprised by slots, and the slots include, therefore, coil anchor and wire anchor reverse engagement surfaces. The engagement surfaces engage the arms upon rotation in the first direction and the reverse engagement surfaces engage the arms upon rotation in the second direction. Thus, the insertion cord stiffener does not rely on tension to bring the anchors together.

Details of the coil anchor 44 are shown in FIGS. 9-11, of which FIG. 9 is a perspective view, FIG. 10 a plan view, and FIG. 11 cross-sectional view A-A of FIG. 10. The coil anchor 44 comprises an annular body 86 with the coil anchor arms 74 extending outwards in radial direction from the annular body 86. The coil anchor arms comprise a rounded abutment face 88 adapted for engagement with the engagement surface 83 of the control ring 62. The coil anchor 44 further comprises a wire opening 90 and a coil opening 92. The wire anchor can be identical to the coil anchor, which would simplify production and assembly, but need not be.

A control ring prototype made up of two segments 94, 96 is depicted in FIG. 12, showing the inside of the control ring segments 94, 96, and revealing the helical engagement surfaces 102, 104. In the assembled state of the endoscope, where the control ring 62 is mounted on the handle 7, as illustrated in FIG. 8, the abutment face 88 of the coil anchor arm 74 abuts the helical engagement surface 104, whereas the wire anchor arm 76 abuts the other helical engagement surface 102. The two helical engagement surfaces 102, 104 of the control ring segment have pitch of opposite direction. If the control ring 62 is twisted as illustrated by the arrow A in FIG. 8, the arm 74 of the coil anchor 44, which is prevented from rotating with the control ring 62, will travel along the helical engagement surface 104, meaning that the coil anchor 44 will be pushed in axial direction (distal direction). At the same time the arm 76 of the wire anchor 46, which is also prevented from rotating with the control ring 62, will travel along the helical engagement surface 102, meaning that the wire anchor 46 will be pushed in the opposite axial direction (proximal direction). Hereby the coil 42 will be put under tension by the wire 45, so the coil 42 is stiffened.

The illustrated control ring prototype is made up of two nearly identical segments, which may be assembled to complete the control ring by engagement of pins 98 of one control ring segment into holes 100 of the other control ring segment. The two control ring segments may be connected along an edge by a hinge, such as a foil hinge, or connected in any other way. For the prototype tape 106 was used to connect the two segments and securely close the control ring around the handle. In principle the control ring could be unitary construction, such as an unbroken ring or as hinged segments of plastic material. The prototype was made for an embodiment comprising anchors having two arms each, and as a consequence the two control ring segments have similar helical engagement surfaces.

The helical engagement surfaces may have a varying pitch, such as to provide a park position 108, 109 for the relaxed state of the stiffener. A first length 110, 111 of the helical engagement surfaces 102, 104 adjacent the park positions 108, 109 has a steep pitch. This gives a quick tensioning of the stiffener, thereby quickly taking up any potential slack of the wire and increasing the stiffness in a part of the process where resistance is relatively low. This also gives a tactile indication to the operator that the variable stiffness function is activated.

The wire anchor engagement surface may comprise a first pitch at an initial position 111a, adjacent the park positions 108, 109, and a second pitch at an end position 111b/c. The first pitch is steep, as indicated above. The second pitch may be substantially less steep than the first pitch. The third pitch may extend from the end of the initial position to the end of the wire anchor engagement surface. The coil anchor engagement surface may be shaped as the wire anchor engagement surface or may be more or less steep.

The wire anchor engagement surface may comprise a first pitch at an initial position 111a, adjacent the park positions 108, 109, a second pitch at an intermediate position 111b, and a third pitch at an end position 111c, the intermediate position being between the initial and the end positions. The first pitch is steep, as indicated above. The second pitch may be substantially less steep than the first pitch. The third pitch may be steeper than the second pitch but less steep than the first pitch, to indicate the end of rotation. The coil anchor engagement surface may be shaped as the wire anchor engagement surface or may be more or less steep.

Figure 13:
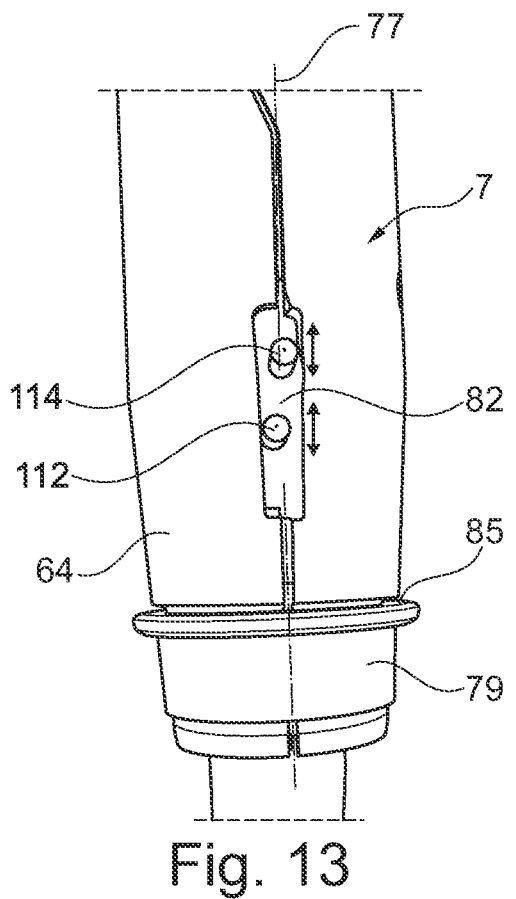
FIG. 13 illustrates a distal part of an endoscope handle according to an embodiment.

As explained, turning the control ring about the handle (counter clock-wise in the illustrated example and with reference to FIG. 8) will force the coil anchor and wire anchor to move away from each other in a translatory movement, as the arms are restricted from turning with the control ring. The arm can for example be restricted from turning by being arranged in a longitudinal slot of the handle, as discussed above with reference to FIG. 8. FIG. 13 illustrates a simple prototype where the longitudinal slot 82 is provided at the split line of the two handle shells 64, which are held together by the hoop 79. For illustration purposes the control ring is not mounted, but if so, it would rest on the proximal shoulder of the hoop 79. The arms of the wire anchor and coil anchor, here in the form of metal pins 112 and 114, extend out through the slot 82 and are restricted to move along the direction of the slot only as indicated by the arrows, so the anchors cannot rotate around the central axis 77 of the handle. In the illustrated example, the slot is provided in the split line between two handle shell parts, which makes it easy to arrange the anchors in one handle shell with arms in the slot and fit the other handle shell on top. In alternative embodiment the slot may be provided at another position than at the split line of two handle shell parts, which could for example give a stronger construction without the arms potentially being urged sideways and thereby forcing the two handle shell parts away from each other.

Figure 14:
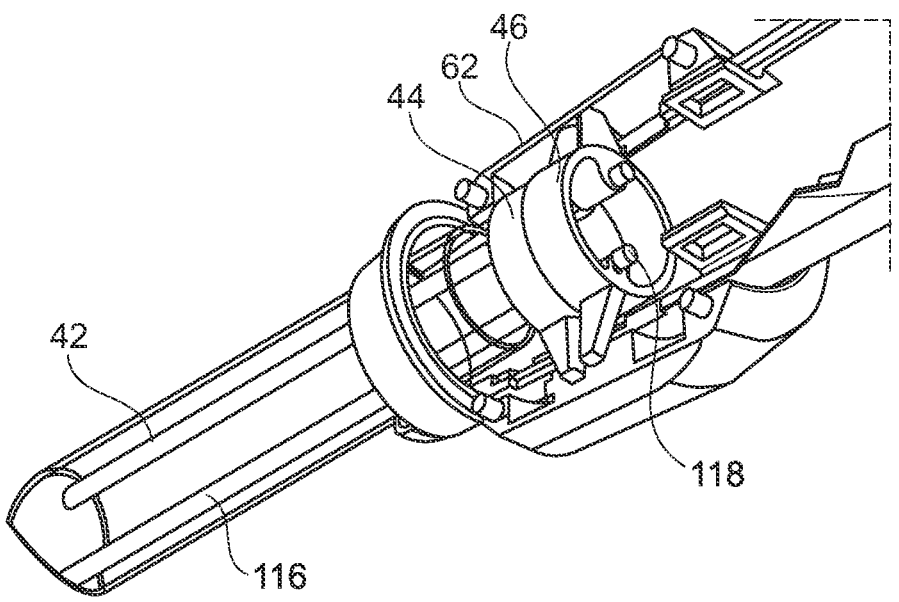
FIG. 14 is a perspective view of an endoscope having two stiffeners, but otherwise corresponding to the endoscope of FIG. 8, FIG. 15A-C illustrate various coil shapes.

FIG. 14 illustrates an embodiment having two stiffeners, i.e. having an extra stiffener comprising a coil 116 and a wire 118, but otherwise identical to the embodiment of FIG. 8. This embodiment provides extra stiffness to the endoscope at a moderate extra cost.

Figures 15A, 15B, 15C:
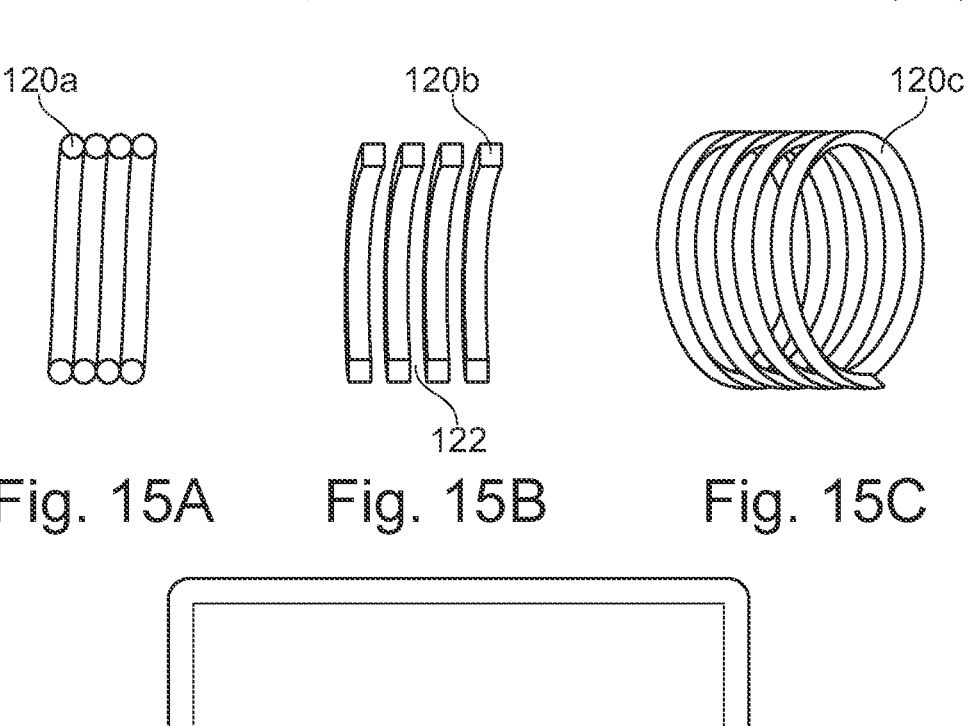

Different shapes and forms of the coil and the wire of the coil can be seen in FIGS. 15A-15C. In FIG. 15A is shown a simple coil made of wires having a circular cross section 120*a*, which would generally be the cheapest type of coil. This coil is made with closely wound wires without a gap between neighbouring wires of the coil. FIG. 15B illustrates an alternative coil made of wires having square cross section 120*b*. This coil is illustrated with a gap 122 between neighbouring wires, but generally it is preferred that the coil does not have a gap. This wire with square cross section will result in a coil which is more stable under compression, as neighbouring wires will join in a flat surface at right angle to the direction of compression, so the risk of neighbouring wires slipping and the coil collapsing is limited. A further variant of the coil made of trapezoid wires 120*c* as seen in FIG. 15C, which again is illustrated with a gap for illustration purposes, although it is preferred that the coil does not have gaps between the windings. This trapezoid wire will result in a coil having a higher bending stiffness. It is preferred that the coil is made up of closely wound wires without gap between neighbouring wires, as a gap would increase the travel needed for the wire to tension the stiffener.

A prototype of the stiffener was made with a coil made of closely wound, round wires of stainless steel 1.4310/SUS 301 with a diameter of 0.4 mm. Diameter of the coil was 1.8 mm. The pull wire of the stiffener was a cable made of 19 strands and had an outer diameter of 0.85 mm.

An insertion cord equipped with this prototype stiffener was tested in a three point bending rig. The test rig had two supports arranged with a distance for supporting the specimen and a piston arranged in the middle for pushing down on the specimen. In the test the supports were arranged to provide a free span for the insertion cord of 100 mm and the piston was controlled to push the insertion cord downwards midway between the supports by 5-10 mm, and the applied force was measured. The insertion cord was arranged to have the measurement at a position at a distance from the end points thereof, specifically around 250 mm from the proximal end. Measurements showed an increase in the necessary force from 10 N to 12-13 N when the stiffener is activated, i.e. with this prototype a stiffness increase of 20-30% of the insertion cord was achieved.

Figure 16:
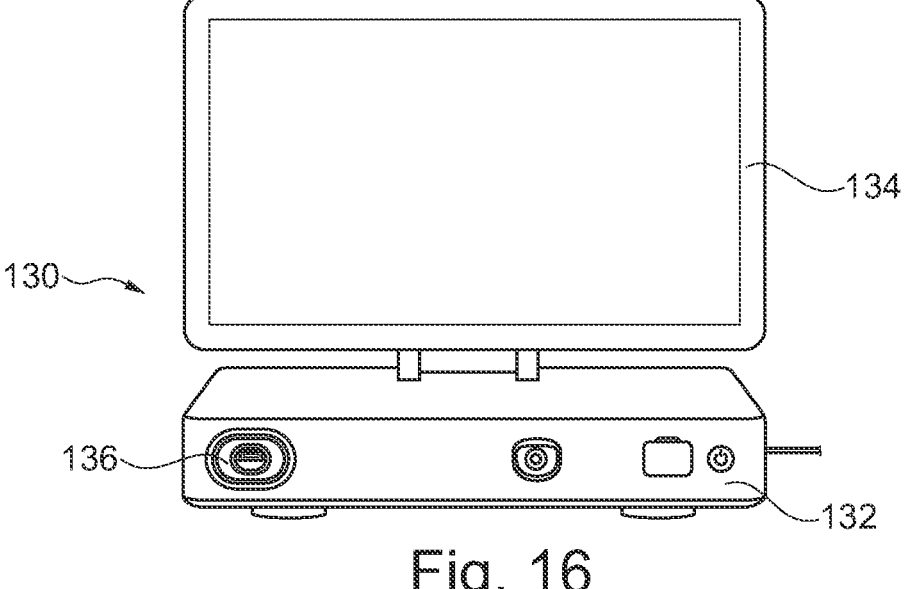
FIG. 16 depicts an example of a video processing apparatus connectable to an endoscope.
Figure 17:
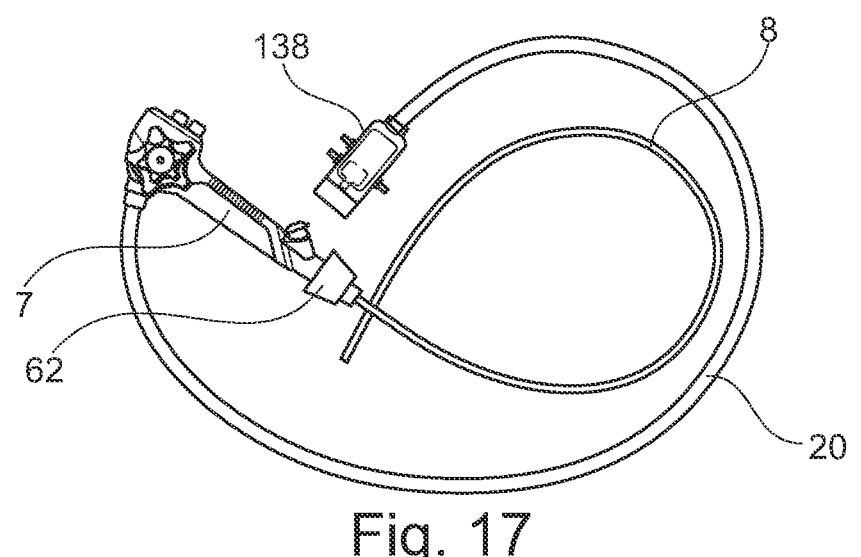
FIG. 17 depicts an example endoscope.

In FIG. 16, an embodiment of a monitor or image processing device, also referred to as video processing apparatus (VPA) 130, is presented. The VPA 130 in the present embodiment includes a housing 132 supporting a display screen 134 and enclosing a video processing circuit (not shown). A cable socket 136 receives an endoscope connector 138 of the endoscope 60 in FIG. 17 to establish a signal communication between the camera 16 and the video processing circuit. The cable socket 136 may be part of, or be connected to, a medical device interface in the VPA 130 which is configured to operate with a particular medical device or endoscope connected thereto. The medical device interface may, for example, process analog or digital image signals, send configuration parameters specific to the camera of the particular endoscope, etc. The cable socket and the connector may comprise markings indicative of specific technologies that compatibilize the medical device interface with the endoscope. The VPA may comprise more than one medical device interface, each potentially operable with different endoscopes. Matching the endoscope with the medial device interface ensures interoperability and tailoring of video processing to the technology of the endoscope. The VPA 130 allows an operator to view an image captured by the camera 16.

Variations of the VPA 130 can be provided with various features of the VPA 130 but including or excluding other features. For example, it might not be desirable to provide a video display screen with a touch screen, or it might be desirable to omit a display screen altogether. Omission of the display screen might be beneficial to take advantage of evolving video display technologies which improve resolution and reduce cost. Provision of exchangeable medical device interfaces allows for adoption of evolving image sensor and endoscope technologies, thus use of existing or future-developed external video displays could allow presentation of higher resolution or otherwise improved video. Use of external video displays could also leverage existing capital investments.

In some variations of the present embodiment, the endoscope and the VPA comprise wireless transceivers to exchange image data and configuration data. The endoscope may comprise a battery to power the camera and the LEDs.

The following items are further variations and examples of the embodiments described with reference to the figures.

1. An endoscope comprising: a handle and an insertion cord extending in a distal direction from the handle; an insertion cord stiffener comprising: a coil with a proximal coil end and a distal coil end, a coil anchor in the handle, a wire anchor at the handle, the proximal coil end abutting the coil anchor and the coil extending into the insertion cord; a wire with a proximal wire end and a distal wire end, the wire extending through the coil and being connected to the coil at the coil distal end, the proximal wire end being connected to a wire anchor; and a stiffener control comprising a rotatable control ring with a rotation axis approximately parallel to the longitudinal direction of the handle, the control ring having an inner side with a helical engagement surface, wherein at least one of the wire anchor or coil anchor comprises at least one anchor arm engaging the helical engagement surface, wherein the handle comprises an anchor guiding surface engaging the at least one of the wire anchor or coil anchor restricting movement thereof to a direction parallel to the rotation axis.

2. The endoscope of item 1, wherein the control ring comprises a proximal helical engagement surface in engagement with the wire anchor and a distal helical engagement surface in engagement with the coil anchor, the proximal and distal engagement surfaces having opposite direction.

3. The endoscope of item 1 or 2, wherein the helical engagement surface has a pitch, which vary along the length of the control ring, such as a first pitch at an initial position and second pitch at an end position, where the first pitch is higher than the second pitch.

4. The endoscope of any one of the items above, wherein the wire anchor and coil anchor each comprises two arms.

5. The endoscope of any one of the items above, wherein the wire anchor is a single-piece construction.

6. The endoscope of any one of the items above, wherein the coil anchor, the wire anchor and the control ring are all made of plastic material.

7. The endoscope of any one of the items above, wherein the coil extends through a majority of the insertion cord, such as more than 50% of the insertion cord, but preferably less than 90%.

8. The endoscope of any one of the items above comprising a second insertion cord stiffener.

9. The endoscope of any one of the items above, wherein the coil is made of a wire having a cross-section selected from circular, rectangular, a parallelogram, trapezoid, or square.

10. The endoscope of any one of the items above, wherein the coil is made of metal.

11. The endoscope of any one of the items above, wherein the wire anchor is arranged proximal to the coil anchor.

12. A visualization system comprising the endoscope of any one of the items above and further comprising an image sensor; and a video processing apparatus capable of processing a video or image signal captured by the image sensor and outputting the processed video or image signal to a coupled display module.

13. Method for manufacturing an endoscope, comprising: providing a first handle shell; providing an insertion cord; providing an insertion cord stiffener comprising a coil, a wire, a wire anchor, a coil anchor and a control ring; arranging the coil to extend into the insertion cord; arranging the coil anchor and the wire anchor in the first handle shell; providing a second handle shell; connecting the second handle shell to the first handle shell; arranging the control ring to encircle the first and second handle shell; and engaging the control ring to at least one of the wire anchor or coil anchor.

LIST OF REFERENCE SIGNS 2 patient
4 operator
6 endoscope
7 handle
8 insertion cord
9 distal tip
10a rectum 10b colon
11, 12 control wheels
14 bending section
16 camera
18 light
19 opening
20 umbilical cord
22 monitor
24 ligaments
26 stiffener
28 coil
30 wire
32 proximal end
34 distal end
36 sleigh
40 stiffener
42 coil
44 coil anchor
45 wire
46 wire anchor
48 distal end
50 proximal end
60 endoscope
62 control ring
64 handle shell
66 Y-connector
68 opening
70 connector
72 connector
74 coil anchor arm
76 wire anchor arm
77 central axis
78 central opening
79 hoop
80 insertion tube
82 slot
83 helical engagement surfaces
84 rotation axis
85 shoulder
86 annular body
88 abutment face
90 wire opening
92 coil opening
94, 96 control ring segments
102, 104 helical engagement surfaces
98 pin
100 hole
106 tape
108, 109 park position
110 first length
111a initial position
111b intermediate position
111c end position
112, 114 metal pin
116 coil
118 wire
120a round cross section
120b square cross section
120c trapezoid wire
122 gap
130 video processing apparatus (VPA)
132 housing
134 display
136 socket
138 connector
A arrow
EV enlarged view
M monitor

We claim:

1. An endoscope comprising:

a handle including a housing wall;

an insertion cord extending in a distal direction from the handle;

a wire including a proximal wire end and a distal wire end;

a coil extending into the insertion cord, the coil including a proximal coil end and a distal coil end;

a coil anchor at the handle, the coil anchor including a coil anchor arm extending radially outwardly through the housing wall, the proximal coil end abutting the coil anchor;

a wire anchor at the handle, the wire anchor including a wire anchor arm extending radially outwardly through the housing wall, the wire extending through the coil and being connected to the wire anchor;

a control ring rotatable about a rotation axis, the control ring including an inner side, a wire anchor engagement surface on the inner side, and a coil anchor engagement surface on the inner side, the wire anchor engagement surface and the coil anchor engagement surface having opposite handedness;

wherein the wire anchor arm engages the wire anchor engagement surface, wherein the coil anchor arm engages the coil anchor engagement surface, and wherein rotation of the control ring about the rotation axis in a first direction separates the coil anchor from the wire anchor along the rotation axis to stiffen the coil.

2. The endoscope of claim 1, wherein the housing wall comprises an anchor guiding surface engaging at least one of the wire anchor arm or the coil anchor arm, to restrict movement of the at least one of the wire anchor arm or the coil anchor arm to a direction parallel to the rotation axis.

3. The endoscope of claim 1, wherein the wire anchor engagement surface includes a proximal end and a distal end, wherein the coil anchor engagement surface includes a proximal end and a distal end, wherein the distal end of the wire anchor engagement surface and the proximal end of the coil anchor engagement surface are closer to each other than the proximal end of the wire anchor engagement surface and the distal end of the coil anchor engagement surface are to each other.

4. The endoscope of claim 1, wherein the housing wall comprises an anchor guiding surface engaging the wire anchor arm and the coil anchor arm, to restrict rotation of the wire anchor and the coil anchor.

5. The endoscope of claim 1, wherein the control ring includes a second wire anchor engagement surface on the inner side and a second coil anchor engagement surface on the inner side, the second wire anchor engagement surface and the second coil anchor engagement surface having opposite handedness; wherein the coil anchor includes a second coil anchor arm extending radially outwardly through the housing wall; wherein the wire anchor includes a second wire anchor arm extending radially outwardly through the housing wall; and wherein the second wire anchor arm engages the second wire anchor engagement surface, and the second coil anchor arm engages the second coil anchor engagement surface.

6. The endoscope of claim 5, wherein the housing wall comprises an anchor guiding surface engaging the wire anchor arm and the coil anchor arm, to restrict rotation of the wire anchor and the coil anchor, and wherein the housing wall comprises a second anchor guiding surface engaging the second wire anchor arm and the second coil anchor arm.

7. The endoscope of claim 6, wherein the handle comprises a first handle shell and a second handle shell, the first handle shell and the second handle shell forming a seam when attached to each other, wherein the handle comprises a first longitudinal slot positioned at the seam and including the anchor guiding surface, and wherein the handle comprises a second longitudinal slot positioned at the seam and including the second anchor guiding surface, the second longitudinal slot positioned opposite the first longitudinal slot.

8. The endoscope of claim 1, wherein the wire anchor engagement surface comprises a first pitch at an initial position and second pitch at an end position, wherein the first pitch is higher than the second pitch, and wherein the end position is adjacent the initial position.

9. The endoscope of claim 1, wherein the wire anchor engagement surface comprises a first pitch at an initial position and a second pitch at an intermediate position, wherein the first pitch is higher than the second pitch.

10. The endoscope of claim 9, wherein the wire anchor engagement surface comprises a third pitch at an end position, wherein the first pitch is higher than the third pitch, and wherein the third pitch is higher than the second pitch.

11. The endoscope of claim 1, wherein the wire anchor is a single-piece construction, wherein the coil anchor is a single-piece construction, and wherein the coil anchor, the wire anchor and the control ring are made of plastic material, and wherein the coil is made of metal.

12. The endoscope of claim 1, wherein the coil extends through a majority of the insertion cord.

13. The endoscope of claim 1, wherein the coil extends through at least 50% but not more than 90% of a length of the insertion cord.

14. The endoscope of claim 1, wherein the wire, the coil, the coil anchor, the wire anchor, and the control ring form an insertion cord stiffener, further comprising a second insertion cord stiffener.

15. The endoscope of claim 1, wherein the wire anchor is arranged proximal to the coil anchor.

16. A visualization system comprising:

the endoscope of claim 1, the endoscope further comprising an image sensor; and a video processing apparatus capable of processing a video or image signal captured by the image sensor and outputting the processed video or image signal to a display module.

17. A method for manufacturing the endoscope of claim 1, the method comprising:

providing a first handle shell;

providing the insertion cord;

providing an insertion cord stiffener comprising the coil, the wire, the wire anchor, the coil anchor and the control ring;

arranging the coil to extend into the insertion cord;

arranging the coil anchor and the wire anchor in the first handle shell;

providing a second handle shell;

connecting the second handle shell to the first handle shell to form the housing;

arranging the control ring to encircle the first handle shell and the second handle shell; and engaging the control ring to the wire anchor and the coil anchor.

* * * * *